US008308647B2

(12) United States Patent
Kolluri et al.

(10) Patent No.: US 8,308,647 B2
(45) Date of Patent: Nov. 13, 2012

(54) SYSTEM AND METHOD FOR A NON-INVASIVE BLOOD PRESSURE MEASUREMENT

(75) Inventors: Sai Kolluri, Mequon, WI (US);
Lawrence Hersh, Milwaukee, WI (US);
Richard Medero, Tampa, FL (US)

(73) Assignee: General Electric Company, Schenectady, NY (US)

( * ) Notice: Subject to any disclaimer, the term of this patent is extended or adjusted under 35 U.S.C. 154(b) by 867 days.

(21) Appl. No.: 12/415,575

(22) Filed: Mar. 31, 2009

(65) Prior Publication Data
US 2010/0249614 A1    Sep. 30, 2010

(51) Int. Cl.
*A61B 5/02*    (2006.01)

(52) U.S. Cl. ..................................................... 600/490

(58) Field of Classification Search ........... 600/300–301, 600/529–543, 481–506
See application file for complete search history.

(56) References Cited

U.S. PATENT DOCUMENTS

| 5,704,362 | A | * | 1/1998 | Hersh et al. | ............. 600/486 |
| 2004/0167411 | A1 | * | 8/2004 | Kolluri et al. | ............. 600/490 |
| 2009/0318828 | A1 | | 12/2009 | Hersh et al. | |

* cited by examiner

*Primary Examiner* — Patricia Mallari
*Assistant Examiner* — Tiffany Weston (57) ABSTRACT

A method of measuring blood pressure of a patient is provided. The method comprises inflating a blood pressure cuff to a user selectable target pressure and subsequently further inflating or deflating the blood pressure cuff in a stepwise manner by a predetermined pressure amount. At each pressure step in a first sequence of alternate steps of cuff pressure variation, the occurrence of at least two successive oscillometric pulses with matching pulse amplitude and other possible matching criteria is identified. The blood pressure cuff is inflated following the identification. Further a single oscillometric pulse is obtained at each pressure step in a second sequence of alternate steps of cuff pressure variation. The pattern of inflating, obtaining two matching oscillometric pulses, inflating, and obtaining a single oscillometric pulse is repeated until sufficient oscillometric envelope information is obtained for determining one or more blood pressure parameters of the patient.

14 Claims, 10 Drawing Sheets

SYSTEM AND METHOD FOR A NON-INVASIVE BLOOD PRESSURE MEASUREMENT

BACKGROUND OF THE INVENTION

The subject matter disclosed herein relates to a system and method for blood pressure measurement. More specifically, the subject matter disclosed herein relates to a system and method for a non-invasive blood pressure measurement that is configured to more accurately and more rapidly estimate one or more blood pressure parameters.

The knowledge of a patient's blood pressure is of great value to those engaged in diagnosis, prognosis and treatment of disease states. In particular, the determination of arterial blood pressure is an essential element in the diagnosis of a patient suspected of having cardiovascular disease. Normal human arterial blood pressure cyclically varies between 80 and 120 mmHg due to the heart beating and moving blood through the vasculature, whereas, for example, elevations of the arterial blood pressure above the specified range, which is known as hypertension, is likely to be found in cases of congestive heart failure.

Non-invasive blood pressure (NIBP) monitors typically inflate a blood pressure cuff, which is wrapped around the upper arm of the patient to a pressure level above the patient's systolic pressure and measure very small amplitude pressure oscillations within the cuff as the cuff is deflated either in steps or continuously. The pressure oscillations in the cuff are due to volume changes resulting from the heart beating and pumping the blood through the arterial system. The amplitude of the cuff pressure oscillations changes as the cuff pressure itself changes. The data set, which describes the cuff oscillation amplitude as a function of the cuff pressure, is commonly known as an oscillometric envelope. The oscillometric envelope obtained from the cuff pressure data is used to determine the patient's blood pressure. The cuff pressure corresponding to the maximum oscillation amplitude is typically taken as the mean arterial pressure (MAP). Systolic and diastolic pressures are computed by finding the cuff pressure levels at which a fixed ratio of the maximum oscillation amplitude occurs. Some NIBP monitors also use details in the shape of the oscillometric envelope to compute the systolic and diastolic pressures.

The cuff pressure data can, in some cases, contain various types of artifacts that may hinder the ability of the NIBP monitor to estimate the blood pressure parameters accurately. Two primary classes of artifacts are patient motion and transient baseline effects. Conventional NIBP techniques are often not capable of handling these artifact problems effectively and this can introduce imprecision into the blood pressure estimates, and may also result in longer determination times, which can be uncomfortable to the patient. Transient baseline effects are well known to those skilled in the art, and may include such phenomena as the heating and cooling of the air within the cuff, the visco-elastic effects of the cuff material which influence the time needed to reach pressure-volume equilibrium, and physiological changes in fluid and tissue volume under the cuff.

Hence there exists a need for providing a method of measuring blood pressure, which enhances the speed of an NIBP monitor without sacrificing accuracy of blood pressure measurement.

BRIEF DESCRIPTION OF THE INVENTION

The above-mentioned shortcomings, disadvantages and problems are addressed herein which will be understood by reading and understanding the following specification.

In one embodiment, a method of monitoring blood pressure is provided. The method comprises obtaining pressure data comprising an oscillatory component and a transient baseline effects component, constructing a waveform of the pressure data, selecting a plurality of data points acquired from the waveform of the pressure data, generating a non-linear transient baseline effects model based on the plurality of data points, implementing the non-linear transient baseline effects model to at least partially deduct the transient baseline effects component from the pressure data such that substantially only the oscillatory component remains and generating an estimate of the blood pressure parameter based on the oscillatory component of the pressure data, wherein the removal of the transient baseline effects component from the pressure data eliminates a potential source of error and thereby enhances the accuracy of the estimated blood pressure parameters. Further the method of obtaining pressure data comprises steps of: (1) inflating a blood pressure cuff to a user selectable target pressure, (2) monitoring for the presence of two substantially similar oscillometric pulses at the user selectable target pressure, (3) deflating the blood pressure cuff upon identification of the occurrence of the oscillometric pulses with a matching criteria, (4) monitoring the presence of a single oscillometric pulse, (5) deflating the blood pressure cuff, and (6) repeating the steps 2-5 until a decision to terminate the pressure data collection is made. Additionally, the method of obtaining pressure data comprises predicting the termination of the deflation of the blood pressure cuff at any particular step when sufficient data has been gathered to estimate the blood pressure parameters so that a decision can be made to obtain one or two oscillometric pulses.

In another embodiment, a method of measuring blood pressure of a patient is provided. The method comprises inflating a blood pressure cuff to a user selectable target pressure and subsequently further inflating the blood pressure cuff in a stepwise manner by a predetermined pressure amount. At each pressure step in a first sequence of alternate steps of the cuff pressure variation, the occurrence of at least two successive oscillometric pulses with matching pulse amplitude and other possible matching criteria is identified. The blood pressure cuff is inflated following the identification of the occurrence of the oscillometric pulses within the criteria. Further a single oscillometric pulse is obtained at each pressure step in a second sequence of alternate steps of the cuff pressure variation. The pattern of inflating, obtaining two matching oscillometric pulses, inflating, and obtaining a single oscillometric pulse is repeated until sufficient oscillometric envelope information is obtained for determining the blood pressure parameters of the patient.

In yet another embodiment, a computer readable storage medium with a plurality of program instructions for execution by a processor of an NIBP monitor so as to monitor blood pressure parameters for a patient is provided. The plurality of program instructions include a routine for obtaining pressure data comprising an oscillatory component and a transient baseline effects component, a routine for constructing a waveform of the pressure data as a function of time, a routine for selecting a plurality of data points acquired from the waveform of the pressure data, a routine for generating a non-linear transient baseline effects model based on the plurality of data points, a routine for implementing the non-linear transient baseline effects model to at least partially deduct the transient baseline effects component from the pressure data such that substantially only the oscillatory component of the pressure data remains and a routine for generating an estimate of the blood pressure parameters based on the oscillatory component of the pressure data, wherein removal of the transient baseline effects component from the pressure data eliminates a potential source of error and thereby enhances the accuracy of the estimated blood pressure parameter.

Further, the routine for obtaining pressure data comprises a routine for inflating a blood pressure cuff to a user selectable target pressure, a routine for monitoring the presence of two substantially similar oscillometric pulses upon achieving the user selectable target pressure, a routine for deflating the blood pressure cuff upon identifying of the occurrence of oscillometric pulses within a matching criteria, a routine for monitoring the presence of a single oscillometric pulse, a routine for deflating the blood pressure cuff, a routine for repeating the steps of obtaining two matched oscillometric pulses, deflating, obtaining one oscillometric pulse and deflating until sufficient data is gathered and a routine for predicting the termination of the deflation of the blood pressure cuff.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
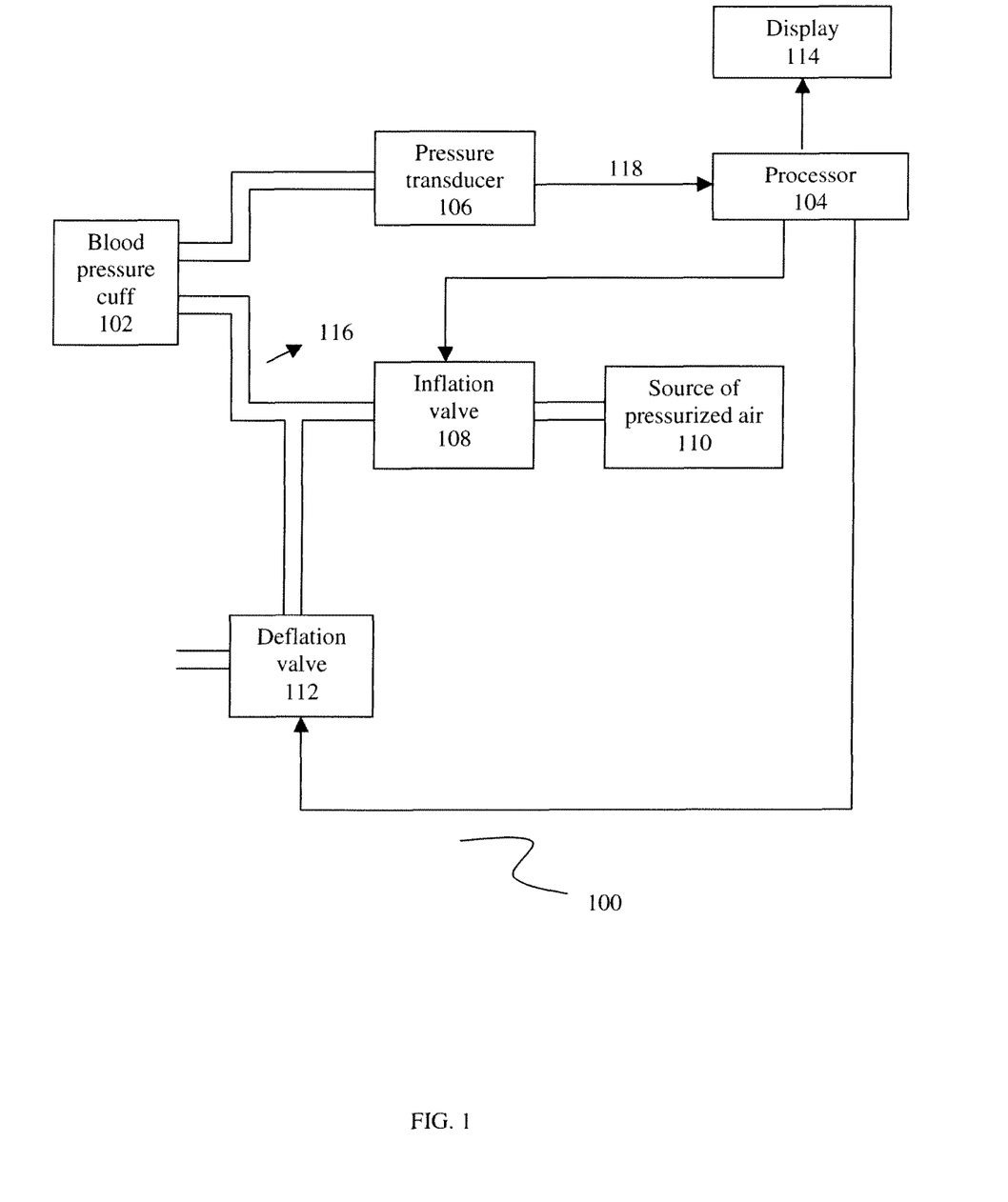
FIG. 1 is a schematic representation of a non-invasive blood pressure monitoring system in accordance with an embodiment.

Referring to FIG. 1, a non-invasive blood pressure (NIBP) monitoring system 100 (referred to hereafter as NIBP system or NIBP monitor) capable of monitoring blood pressure in a patient is shown in accordance with an embodiment. The NIBP system 100 includes an inflatable and deflatable blood pressure cuff 102, a processor 104, a pressure transducer 106, an inflation valve 108, a source of pressurized air 110, a deflation valve 112 and a display 114. In the embodiment depicted, the blood pressure cuff 102 is wrapped around the patient's upper arm, however other locations (e.g., forearm, wrist, finger) and other limbs may also be used. The blood pressure cuff 102 herein after referred to as the cuff 102 or pressure cuff 102 can be inflated and deflated for occluding or partially occluding the brachial artery of the patient when in fully or partially inflated condition. The blood pressure cuff 102 is pneumatically coupled with the pressure transducer 106, the inflation valve 108 and the deflation valve 112 via a flexible tube 116. The processor 104 is electronically coupled to the pressure transducer 106, the inflation valve 108, the deflation valve 112 and the display 114.

The processor 104 is configured to coordinate the operation of valves 108 and 112, in a manner adapted to regulate cuff inflation and deflation. More precisely, the processor 104 can selectively open the inflation valve 108 in order to allow the source of pressurized air 110 to inflate the cuff 102, and selectively open the deflation valve 112 to release the pressurized air 110 and thereby deflate the cuff 102.

In accordance with general oscillometric techniques, the pressure transducer 106 is used to sense oscillometric pulses in the cuff 102 that are generated by pressure-volume changes in the brachial artery positioned under the cuff 102. The oscillometric pulses are embedded in the electronic waveform representing the cuff pressure, as converted by the pressure transducer 106, and are obtained by the processor 104, using an analog-to digital converter, through a connection line 118.

Figure 2:
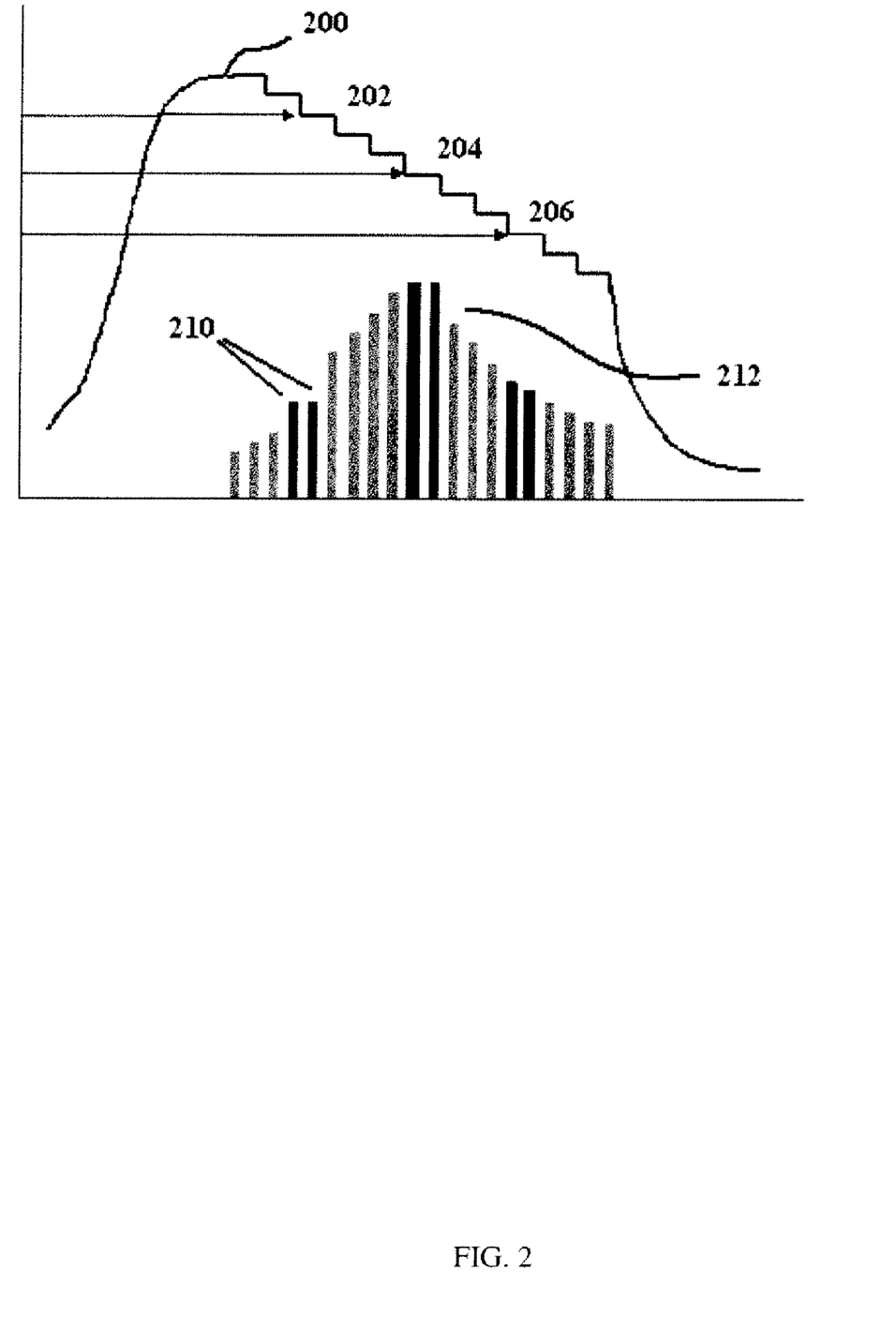
FIG. 2 is a graph of cuff pressure versus time depicting an oscillometric envelope.

The oscillometric pulses are collectively named as pressure data. The processor 104 is configured to estimate a blood pressure parameter such as mean arterial pressure (MAP), systolic blood pressure (SBP), and/or diastolic blood pressure (DBP) based on the pressure data from the pressure transducer 106. The processor 104 is also configured to transmit the estimated MAP, SBP and/or DBP values to the display 114. The display 114 is configured to visually convey the estimated MAP, SBP and/or DBP values. With reference to FIG. 1 and FIG. 2, an exemplary process of estimating SBP 202, MAP 204, and DBP 206 will be described in accordance with several embodiments.

The exemplary process of estimating MAP 204, SBP 202 and/or DBP 206 is performed by varying the pressure of the cuff 102 in a manner illustrated by the cuff pressure curve 200 of FIG. 2, and simultaneously measuring a series of oscillometric pulses 210. A curve, which is a collective representation of the amplitudes of the oscillometric pulses 210, as a function of cuff pressure, is typically referred to as the oscillometric envelope 212.

Figure 3:
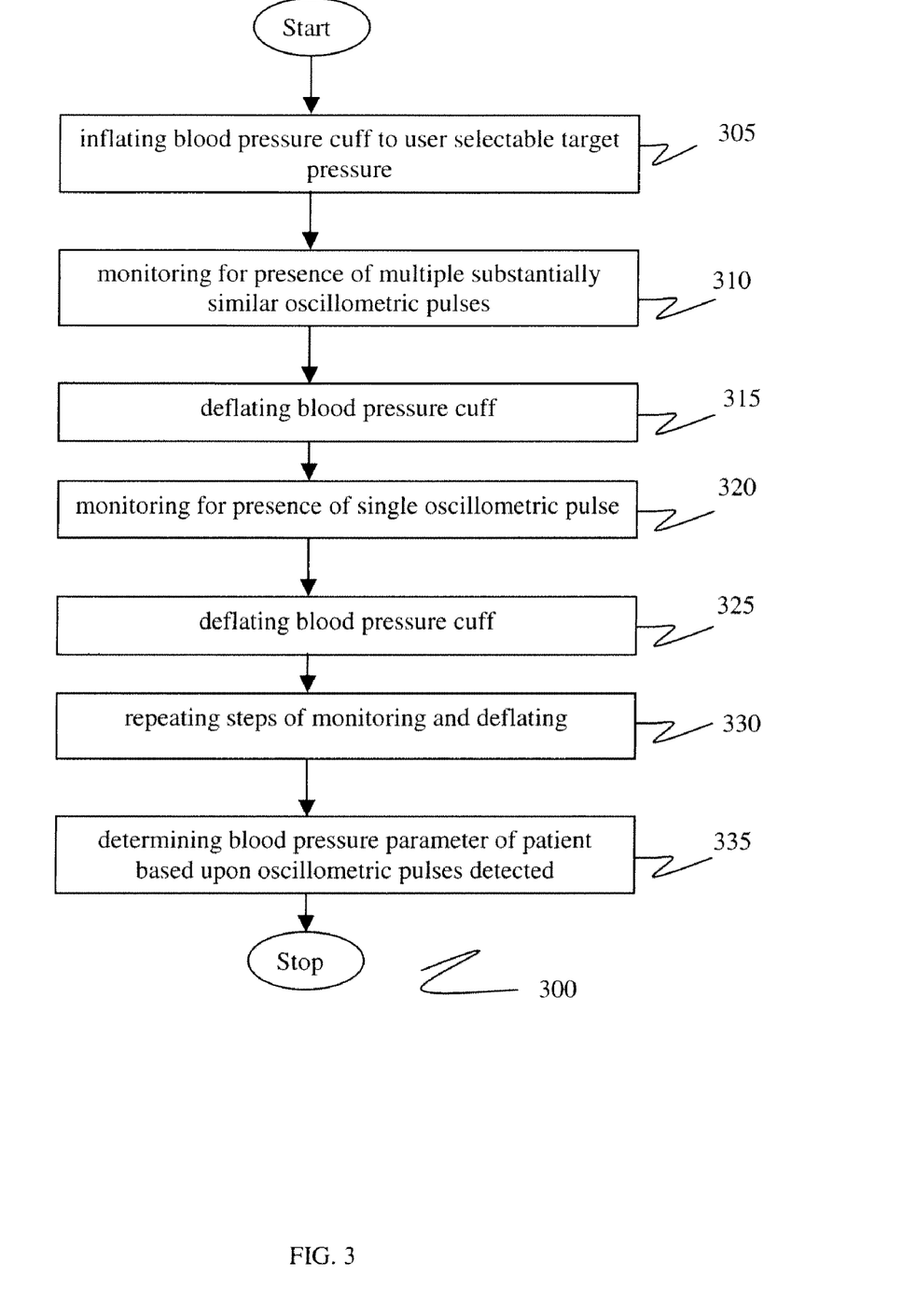
FIG. 3 is a flowchart illustrating the detailed method of estimating the blood pressure of a patient using an oscillometric technique as is described in an embodiment.

A method 300 of monitoring blood pressure, as described by the flowchart in FIG. 3, is initiated by inflating the cuff 102 to a user selectable target pressure that is typically a supra-systolic pressure level, step 305. As is known in the art, at supra-systolic cuff pressure, blood is completely occluded or obstructed from flowing through the artery under the cuff 102, systolic pressure is the cuff pressure level at which blood just begins flowing through the artery under the cuff 102, and diastolic pressure is the cuff pressure level at which blood flow through the artery under the cuff 102 is unobstructed. Following the increment of the cuff pressure to a supra-systolic pressure level, the cuff 102 is deflated (via the deflation valve 112) in a controlled manner adapted to produce a series of decreasing pressure levels referred to hereafter as pressure steps. However, pressure step may also include a series of increasing pressure levels. It should be appreciated that while the exemplary embodiment has been described and depicted as including a stepwise cuff pressure reduction, other embodiments may alternately implement a generally continuous cuff pressure reduction. Additional possible embodiments include other cuff inflation and deflation patterns.

Subsequent to the cuff pressure reaching the systolic pressure, the pressure level measured by the pressure transducer 106 oscillates due to the force generated by the entry of blood into the artery under the cuff 102. The term "oscillation" refers to a measurable pressure level oscillometric pulse produced by this change in blood volume.

Two consecutive oscillometric pulses are generally measured at each alternate cuff pressure step to guarantee consistency in the measurement of the pulse properties for that pressure step and thereby reject artifacts, as described at step 310. Two consecutive oscillometric pulses are defined as substantially similar by having a consistent pulse shape, pulse period and pulse amplitude. Thus, the processor 104 is configured to not only reject pulses when their peak to peak value is of a non-acceptable tolerance, it can as well reject pulses by evaluating their shape, for example how fast or how slow they reach their peak.

The blood pressure cuff 102 is deflated following the identification of the occurrence of the oscillometric pulses within the criteria at step 315. Further, at each alternate pressure step, a single oscillometric pulse is recorded as described at step 320. Following the identification of the single oscillometric pulse, the cuff 102 is further deflated by a predetermined pressure amount at step 325. The process of deflation and identification of the oscillometric pulses is repeated until a decision to terminate the pressure data collection is made at step 330. Subsequently, the deflation of the cuff 102 is terminated and the blood pressure parameter is determined based on the oscillometric pulses detected at step 335. As shown in FIG. 2, MAP 204 is identifiable as the cuff pressure level at which amplitude of the oscillometric pulse is maximum ($OA_{max}$). SBP 202 is identifiable as the cuff pressure level at which amplitude of the oscillometric pulse is approximately equal to $(0.5*(OA_{max}))$, and DBP 206 is identifiable as the cuff pressure level at which amplitude of the oscillometric pulse is approximately equal to $(0.625*(OA_{max}))$. The actual fractions of $OA_{max}$ used to generate systolic and diastolic blood pressure estimates depends upon the signal processing implemented and can be further influenced by the experience of those skilled in the art of oscillometry.

In an alternate embodiment, the method may comprise inflating the blood pressure cuff 102 to a user selectable target pressure, monitoring for the presence of two substantially similar oscillometric pulses, subsequently inflating or deflating the blood pressure cuff 102 based upon the information needed to complete the oscillometric envelope 212, monitoring the presence of a single oscillometric pulse, varying the pressure in the blood pressure cuff 102 further based upon the information needed to complete the oscillometric envelope 212, repeating the steps of monitoring and inflating or deflating the blood pressure cuff, in a variety of combinations until a decision to terminate the pressure data collection is made and determining the blood pressure parameters of the patient based upon the oscillometric pulses detected.

Figure 4:
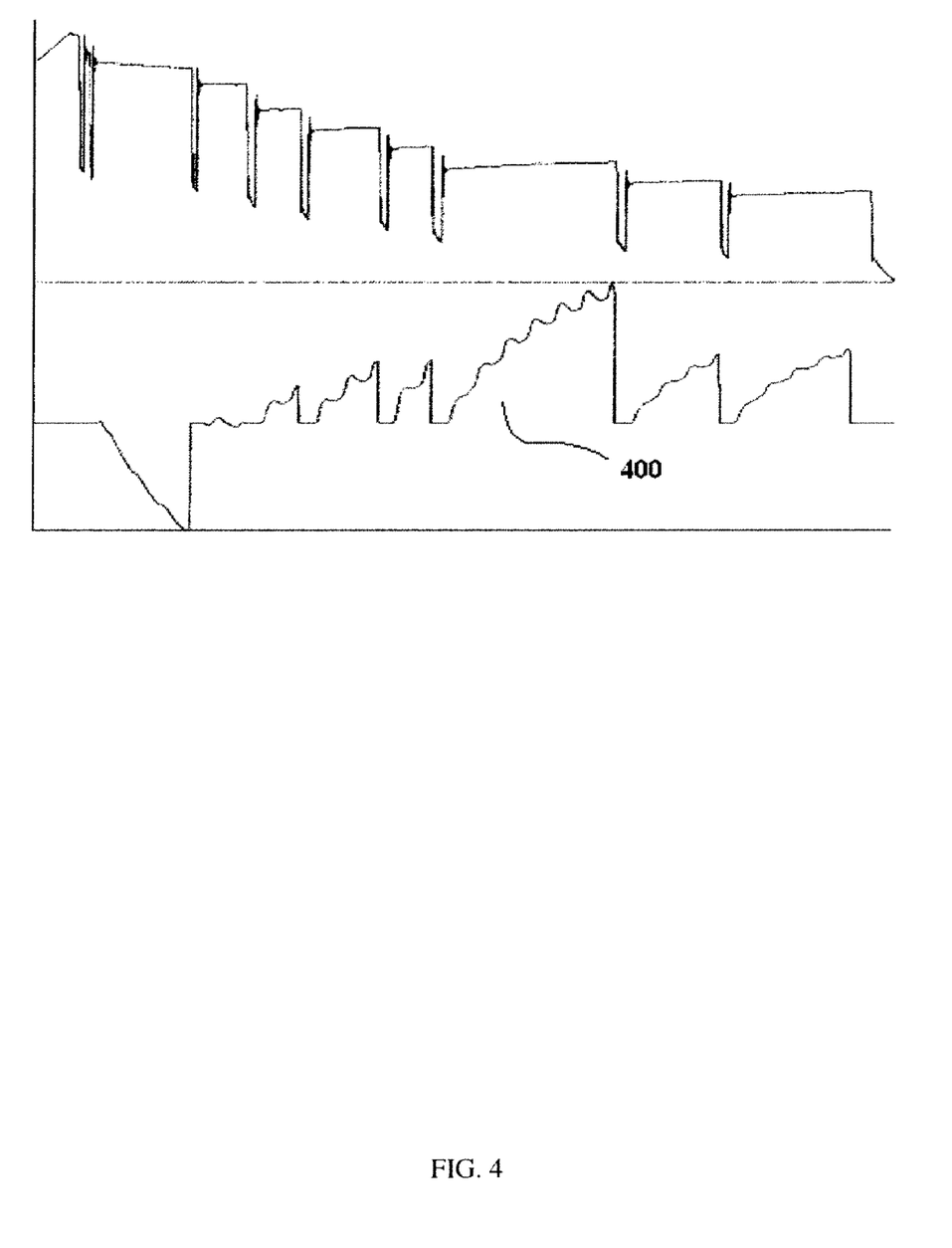
FIG. 4 is a graph of the pressure data waveform along with that of an amplified and band-pass filtered version of the pressure data waveform.

In one embodiment, conventional digital filter techniques may be used to yield oscillometric pulses corresponding to each heartbeat. Upon receiving the filtered signal, the processor 104 is able to detect the oscillometric pulses present during the inflation or deflation of the blood pressure cuff 102. Referring to FIG. 4, a waveform 400 is shown representing filtered pressure data acquired from the pressure transducer 106 during one of the pressure steps (shown in FIG. 2). Filtering is implemented to more clearly identify the constituent parts of the pressure data, and it should be appreciated that there are a variety of filtering methods that may be implemented for this purpose. In one embodiment, the pressure data waveform may be amplified and band-pass filtered. The depicted portion of the waveform 400 comprises an oscillatory component attributable to the patient's cardiac activity and a transient baseline effects component.

Figure 5:
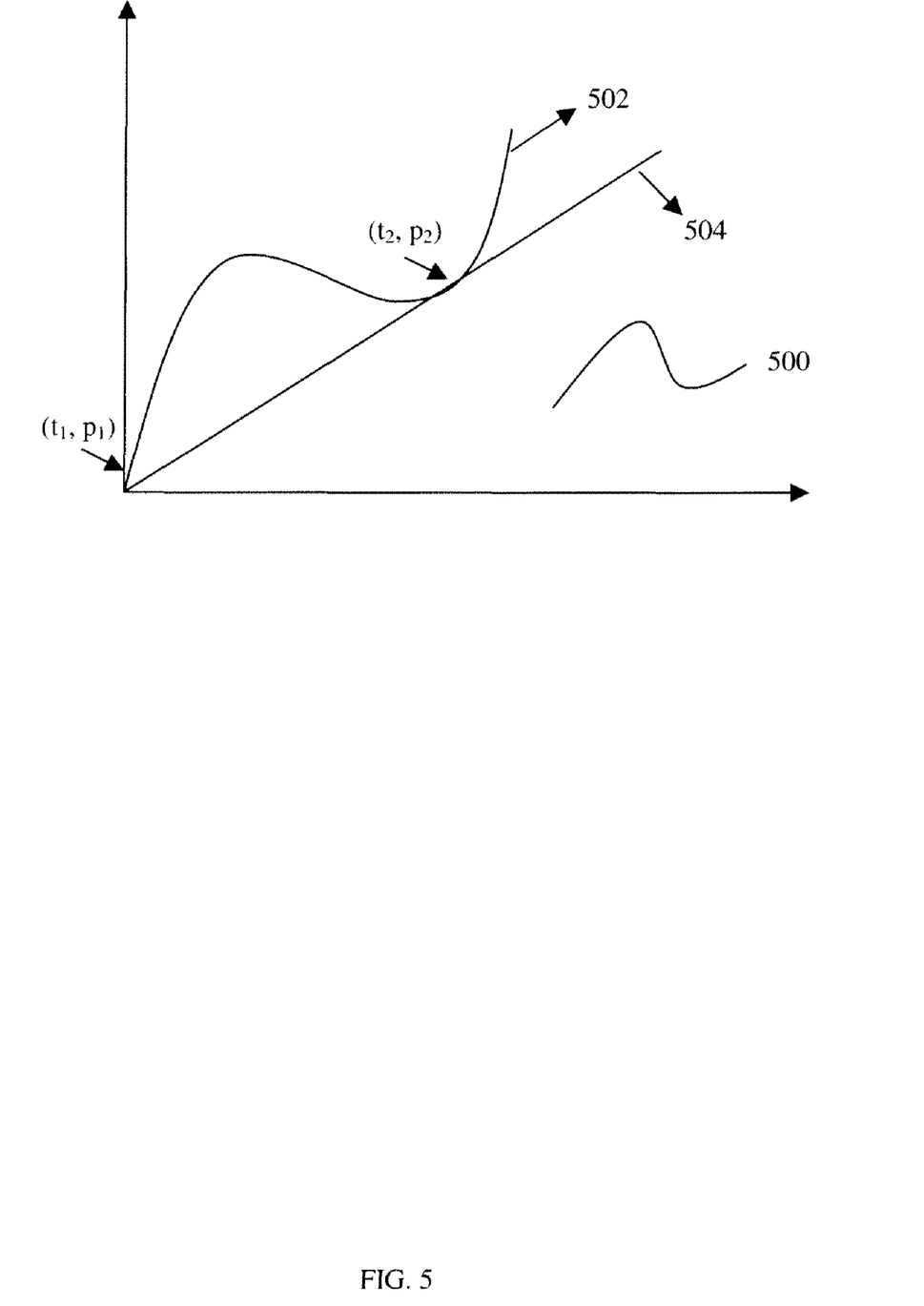
FIG. 5 is an exemplary waveform of a part of the pressure data comprising an oscillatory component and a transient baseline effects component obtained at a single pressure step.

FIG. 5 shows an exemplary waveform 500 of pressure data 502 comprising an oscillatory component and a transient baseline effects component 504. While shown and described hereinafter as producing a steadily increasing pressure level, the transient baseline effects component 504 may alternatively cause the pressure level to decrease during some of the steps of cuff pressure variation.

It should be appreciated that the transient baseline effects component 504 of the waveform 500 is responsible for introducing imprecision into the MAP 204, SBP 202 and DBP 206 estimates. The transient baseline effects 504 can vary the pressure data acquired by the pressure transducer 106 at each pressure step, and can also complicate the process of detecting and measuring oscillometric pulse property details. This pressure data variation correspondingly varies the oscillometric pulse amplitude measurements and the resultant MAP 204, SBP 202 and DBP 206 estimates. In a non-limiting manner, the transient baseline effects may include any effect caused by the heating and/or cooling of air within the cuff 102, the visco-elastic properties of the cuff material, and any physiological changes in fluid volume or tissue response under the cuff 102. Transient baseline effects are well known to those skilled in the art and therefore will not be described in detail.

Accordingly, as will be described in detail hereinafter, the transient baseline effects component 504 may be modeled or otherwise approximated and thereafter subtracted from the pressure data such that substantially only the oscillatory component remains. Thereafter, the oscillatory component may be implemented to estimate MAP 204, SBP 202 and DBP 206 in a manner that minimizes the imprecision associated with the transient baseline effects component 504.

Figure 6:
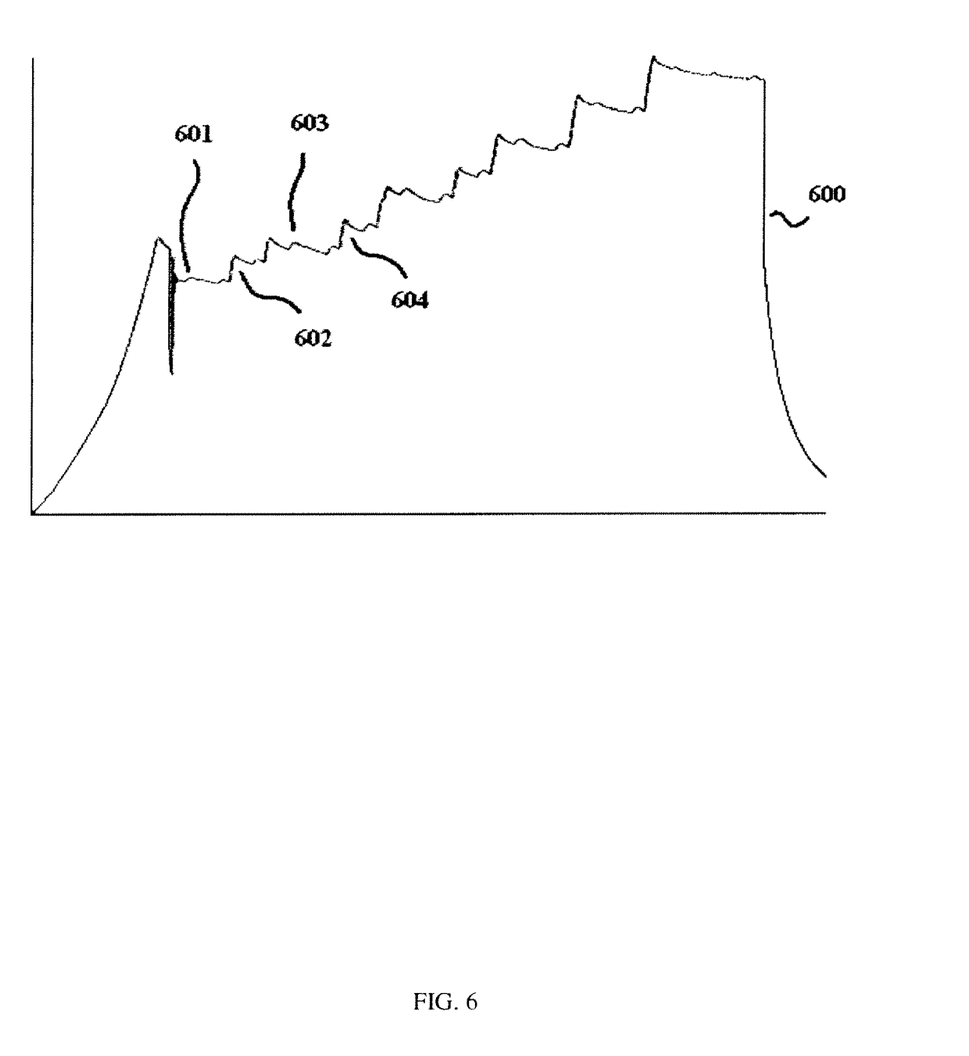
FIG. 6 is a waveform of the pressure data with oscillometric pulses as described in an embodiment of the invention.

FIG. 6 shows an exemplary waveform 600 of the pressure data obtained during a step inflation process. The step inflation is a process where the pressure data is obtained during variation of the cuff pressure in a stepwise increasing manner. Contrary to this, step deflation is a process where the pressure data is obtained during variation of the cuff pressure in a stepwise decreasing manner. The pressure data shown at FIG. 6 is a collection of plurality of oscillometric pulses obtained during plurality of pressure steps such as 601, 602, 603 and 604. The pressure steps 601 and 603 represent steps with plurality of oscillometric pulses and the pressure steps 602 and 604 represent alternate pressure steps with a single oscillometric pulse. Each oscillometric pulse is a collection of plurality of data points. The data points constituting each of the plurality of oscillometric pulses obtained during the pressure steps 601 and 603 are termed hereafter as primary data points. The data points constituting the single oscillometric pulse obtained during the pressure steps 602 and 604 are termed as secondary data points.

As can be seen from FIG. 6, the pressure data comprises oscillometric pulses obtained from several pressure steps including the oscillometric pulses obtained during the four pressure steps 601, 602, 603 and 604. Accordingly, the data points constituting each of a plurality of oscillometric pulses obtained during a single pressure step are termed hereafter as primary data points. Similarly, the data points constituting a single oscillometric pulse obtained during a single pressure step are termed hereafter as secondary data points.

Figure 7:
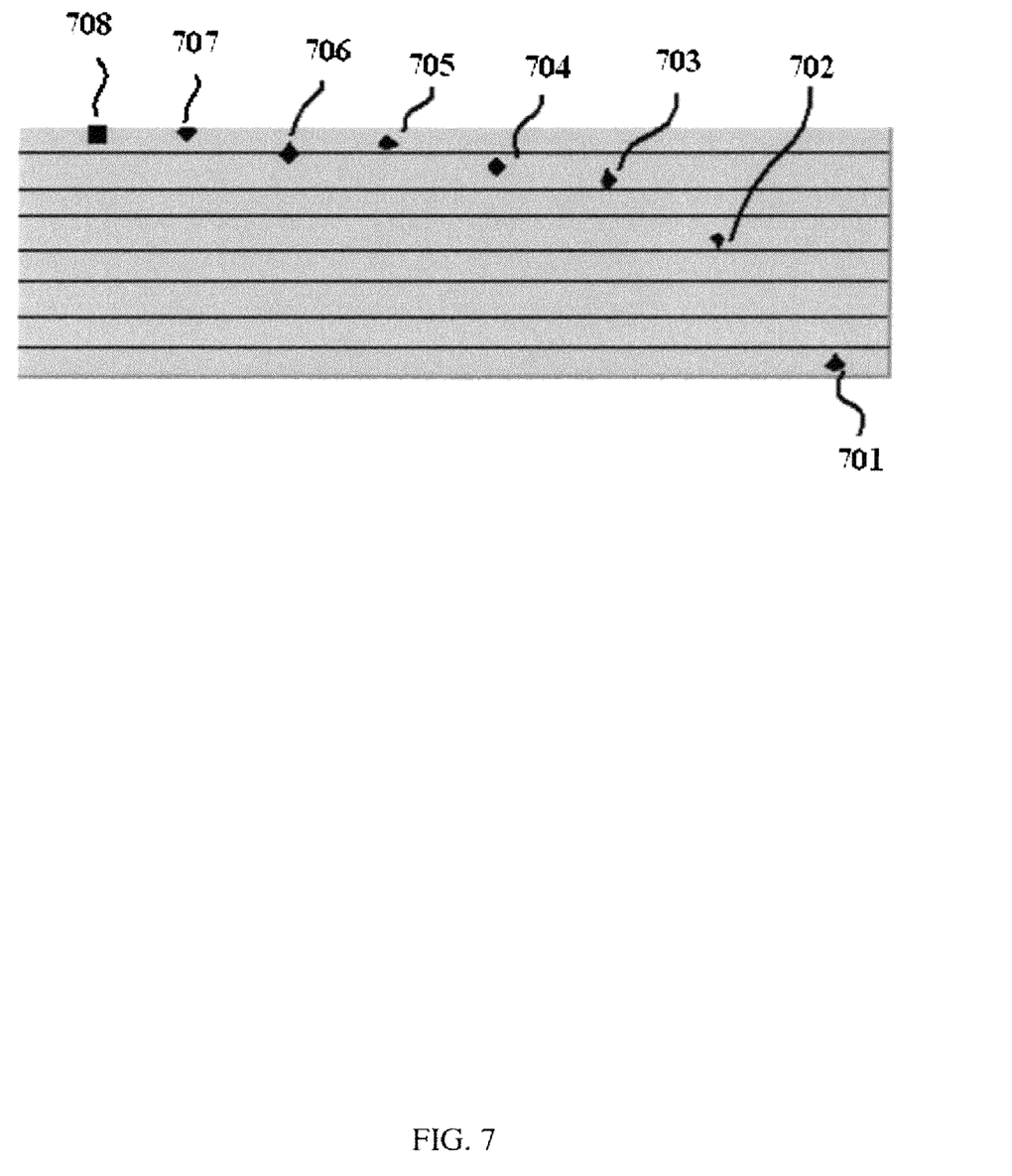
FIG. 7 is a plot of the transient baseline effects component versus cuff pressure established using the transient baseline effects model described in the prior art.

FIG. 7 shows a series of transient baseline effects components 701, 702, 703, 704, 705, 706, 707 and 708 estimated for the oscillometric pulses obtained at different cuff pressures during a typical NIBP determination. The transient baseline effects components 701, 702, 703, 704, 705, 706, 707 and 708 plotted on this graph correspond to the pressure data collected by the NIBP system 100 by performing a step deflation of the cuff pressure and gathering more than one oscillometric pulse at each pressure step. The transient baseline effect components 701, 702, 703, 704, 705, 706, 707 and 708 are computed using techniques described in the art.

As can be understood from the graph of FIG. 7, the transient baseline effects component versus cuff pressure characteristic has a sharp rise and then flattens, as the pressure is step deflated, during this exemplary determination. A method of generating the transient baseline effects model makes an assumption that the characteristic of the transient baseline effects component would be similar had the NIBP determination obtained a single oscillometric pulse at alternate pressure steps.

The transient baseline effects component can be modeled or estimated in a variety of different ways. The following describes an embodiment wherein the processor 104 (shown in FIG. 1) generates an exponential transient baseline effects model as an estimate of the transient baseline effects component. It should, however, be appreciated that the transient baseline effects component may alternately be modeled based on other types of equations such as, for example, a polynomial equation.

Referring to FIG. 5, the transient baseline effects model is initially established by implementing the processor 104 to identify one or more primary data points $(t_1, p_1)$ and $(t_2, p_2)$ that are common to both the pressure data 502 and the transient baseline effects model 504. In one embodiment, the primary data points $(t_1, p_1)$ and $(t_2, p_2)$ are defined as consecutive relative minimum values of the pressure data 502 which indicate the approximate start of the oscillometric pulses for that pressure step. The selection of relative minimum values is convenient in that they are generally easy to identify, however, it should be appreciated that any other consistent phase points (e.g., relative maximum values, some other means of identifying the start of the oscillometric pulse, or some pressure data points that have the same relative position within each oscillometric pulse) of the waveform 502 may alternatively be used to establish the transient baseline effects model.

Following the identification of the primary data points $(t_1, p_1)$ and $(t_2, p_2)$, the transient baseline effects components for each of the primary data points can be estimated by the processor 104 using a non-linear exponential equation: $P_t = Ae^{-(t-t_1)/T} + B$. The variable $P_t$ represents the pressure of the transient baseline effects model at time t, the variable A represents the magnitude of the change in the transient baseline effects model, the variable B represents the equilibrium or steady state pressure of the transient baseline effects model, and the variable T is a time constant. Alternative embodiments may generate a transient baseline effects model based on any line or curve incorporating the points $(t_1, p_1)$ and $(t_2, p_2)$.

The exponential equation $P_t = Ae^{-(t-t_1)/T} + B$ can be specified by setting up and solving a two equation and two unknown system in the following manner. The first equation is obtained by evaluating the exponential equation at time $t_1$ such that $t = t_1$ and $P_t = p_1$, and solving for B. The first equation becomes: $B = p_1 - A$. The second equation is obtained by evaluating the exponential equation at time $t_2$ such that $t = t_2$ and $P_t = p_2$, replacing the variable B with the quantity $(p_1 - A)$ as per the first equation, and solving for A. The second equation becomes $$A = \frac{(p_1 - p_2)}{1 - e^{\frac{-(t_2-t_1)}{T}}}.$$

Experimentation based on a variety of transient baseline effects models has revealed that the time constant T is generally approximately equal to one second. In summary, the transient baseline effects component can be determined algebraically by setting the time constant T as equal to one second, using the points $(t_1, p_1)$ and $(t_2, p_2)$, and assuming a simple exponential form. This yields two equations and two unknowns such that the variables A and B of the exponential equation can be obtained. Alternatively, the variables A, B and T can all be obtained by the additional use of a third primary data point $(t_3, p_3)$ with the same phase position from the waveform, and evaluating the exponential equation at time $t_3$ to specify a third equation, such that there are three equations and three unknowns.

Subsequent to solving for or otherwise obtaining values for A, B and T, the exponential equation is solvable to estimate the transient baseline effects component for each of the primary data points. The method disclosed above to estimate the transient baseline effects component for the primary data points requires two baseline points at the beginning of the oscillometric pulses on each pressure step. This technique cannot be used for estimating the transient baseline effects component for the secondary data points as only one baseline point is obtained at the beginning of the oscillometric pulse. However, the transient baseline effects components estimated for the primary data points can be employed for determining the transient baseline effects components for the secondary data points. This is further explained in conjunction with FIG. 8.

Figure 8:
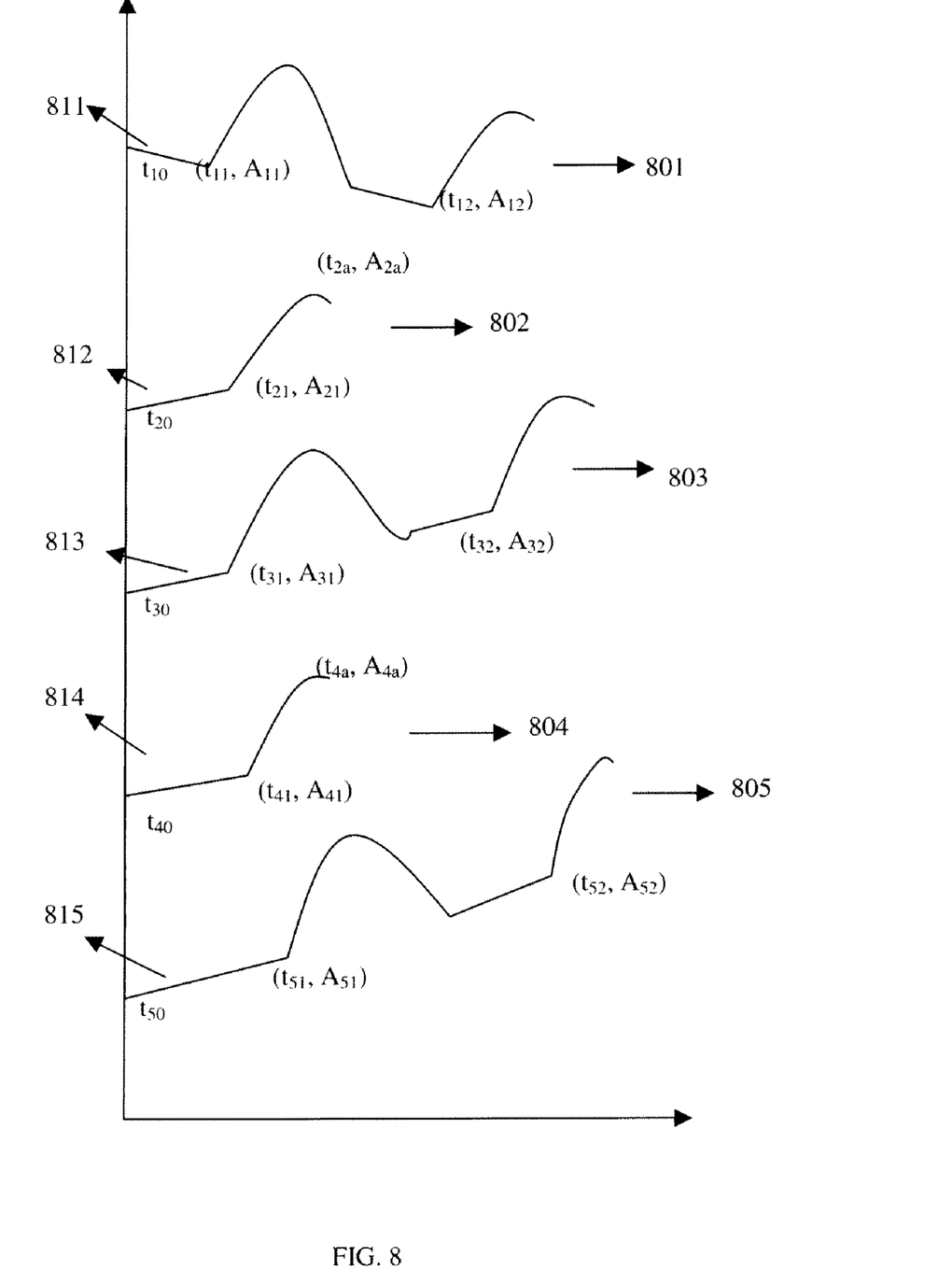
FIG. 8 shows a series of waveforms representing the oscillometric pulses obtained during five consecutive pressure steps.

FIG. 8 shows a series of waveforms representing the oscillometric pulses obtained during five consecutive pressure steps 801, 802, 803, 804 and 805. The pressure steps 801, 803 and 805 represent steps with plurality of oscillometric pulses and the pressure steps 802 and 804 represent alternate pressure steps with a single oscillometric pulse. The data points $(t_{11}, A_{11})$, $(t_{12}, A_{12})$, $(t_{31}, A_{31})$, $(t_{32}, A_{32})$, $(t_{51}, A_{51})$ and $(t_{52}, A_{52})$ constituting part of the plurality of oscillometric pulses obtained during each of the pressure steps 801, 803 and 805 represent the primary data points and the data points $(t_{21}, A_{21})$, $(t_{2a}, A_{2a})$, $(t_{41}, A_{41})$, $(t_{4a}, A_{4a})$ constituting part of the single oscillometric pulse obtained during pressure steps 802 and 804 represent the secondary data points. Further, 811, 812, 813, 814 and 815 respectively correspond to the transient baseline effects components estimated for the oscillometric pulses obtained at pressure steps 801, 802, 803, 804 and 805.

In the embodiment where the pressure cuff 102 is deflated stepwise for obtaining the pressure data, as can be seen from FIG. 8, the transient baseline effects component 812 for the secondary data point $(t_{21}, A_{21})$ is typically closer to the transient baseline effects component 813 for the primary data point $(t_{31}, A_{31})$ than to the transient baseline affects component 811 for the primary data point $(t_{11}, A_{11})$. This is attributed to a change in the direction of the transient baseline effects model from the primary data point $(t_{11}, A_{11})$ to the primary data point $(t_{31}, A_{31})$. Therefore, a first weighting equation is employed to estimate the transient baseline effects component 812 associated with the secondary data point $(t_{21}, A_{21})$.

Thus, the transient baseline effects component 812 for the first secondary data point $(t_{21}, A_{21})$ can be determined using the first weighting equation:

$$A_{2a} - A_{21} = A_2 \left( e^{\frac{-(t_{2a}-t_{20})}{T}} - e^{\frac{-(t_{21}-t_{20})}{T}} \right)$$

where $$A_2 = \frac{\left[ \frac{A_{11} - A_{12}}{\left(e^{\frac{-(t_{11}-t_{10})}{T}} - e^{\frac{-(t_{12}-t_{10})}{T}}\right)} \times e^{\frac{-(t_{20}-t_{10})}{T}} + \frac{A_{31} - A_{32}}{\left(e^{\frac{-(t_{31}-t_{30})}{T}} - e^{\frac{-(t_{32}-t_{30})}{T}}\right)} \times \frac{1}{1 + e^{\frac{-(t_{30}-t_{20})}{T}}} \right]}{e^{\frac{-(t_{20}-t_{10})}{T}} + \frac{1}{1 + e^{\frac{-(t_{30}-t_{20})}{T}}}}$$

Note that the first weighting equation weights the information about the transient baseline effect component 811 for the primary data point $(t_{11}, A_{11})$ preceding the first secondary data point $(t_{21}, A_{21})$ and the transient baseline effect component 813 for the primary data point $(t_{31}, A_{31})$ succeeding the first secondary data point $(t_{21}, A_{21})$ to help make the adjustment for the transient baseline effects component 812 corresponding to the first secondary data point $(t_{21}, A_{21})$.

The transient baseline effects component 814 for the subsequent secondary data point $(t_{41}, A_{41})$ can be estimated using a second weighting equation:

$$A_{4a} - A_{41} = A_4 \left( e^{\frac{-(t_{4a}-t_{40})}{T}} - e^{\frac{-(t_{41}-t_{40})}{T}} \right)$$

where $$A_4 = \frac{\left[ \frac{A_{31} - A_{32}}{\left(e^{\frac{-(t_{31}-t_{30})}{T}} - e^{\frac{-(t_{32}-t_{30})}{T}}\right)} + \frac{A_{51} - A_{52}}{\left(e^{\frac{-(t_{51}-t_{50})}{T}} - e^{\frac{-(t_{52}-t_{50})}{T}}\right)} \right]}{2}$$

Thus, the second weighting equation is used to estimate the transient baseline effects component for all the secondary data points succeeding the first secondary data point $(t_{21}, A_{21})$. Note that the second weighting equation weights the information about the transient baseline effects component 813 for the primary data point $(t_{31}, A_{31})$ preceding the secondary data point $(t_{41}, A_{41})$ and the transient baseline effects component 815 for the primary data point $(t_{51}, A_{51})$ succeeding the secondary data point $(t_{41}, A_{41})$ to help make adjustment for the estimation of the transient baseline effects component 814 corresponding to the secondary data point $(t_{41}, A_{41})$.

In another embodiment, for the NIBP monitor 100 that does step inflation, the transient baseline effects component versus cuff pressure characteristic is in a single direction with each pressure step increment. Therefore, the transient baseline effects component for the first secondary data point $(t_{21}, A_{21})$ and the subsequent secondary data points $(t_{41}, A_{41})$ can be computed using the second weighting equation.

Subsequent to solving for or otherwise obtaining values for A, B and T, the first and the second weighting equations are able to estimate the transient baseline effects components for the secondary data points. Thus, the exponential equation along with the first and second weighting equations can be used to completely define the transient baseline effects model. Thereafter, the complete transient baseline effects model or any portion thereof can be removed (i.e., subtracted) from the pressure data in order to eliminate or at least minimize the inaccuracy or imprecision introduced by the transient baseline effects. It should be appreciated that the elimination or minimization of the errors introduced by the transient baseline effects, in the manner described above, provides a more accurate and precise estimate of MAP 204, SBP 202, and DBP 206.

In another embodiment, the invention further describes a method to identify the pressure steps scheduled for obtaining a single oscillometric pulse and also a method to predict the termination of the cuff pressure variation.

Figure 9A:
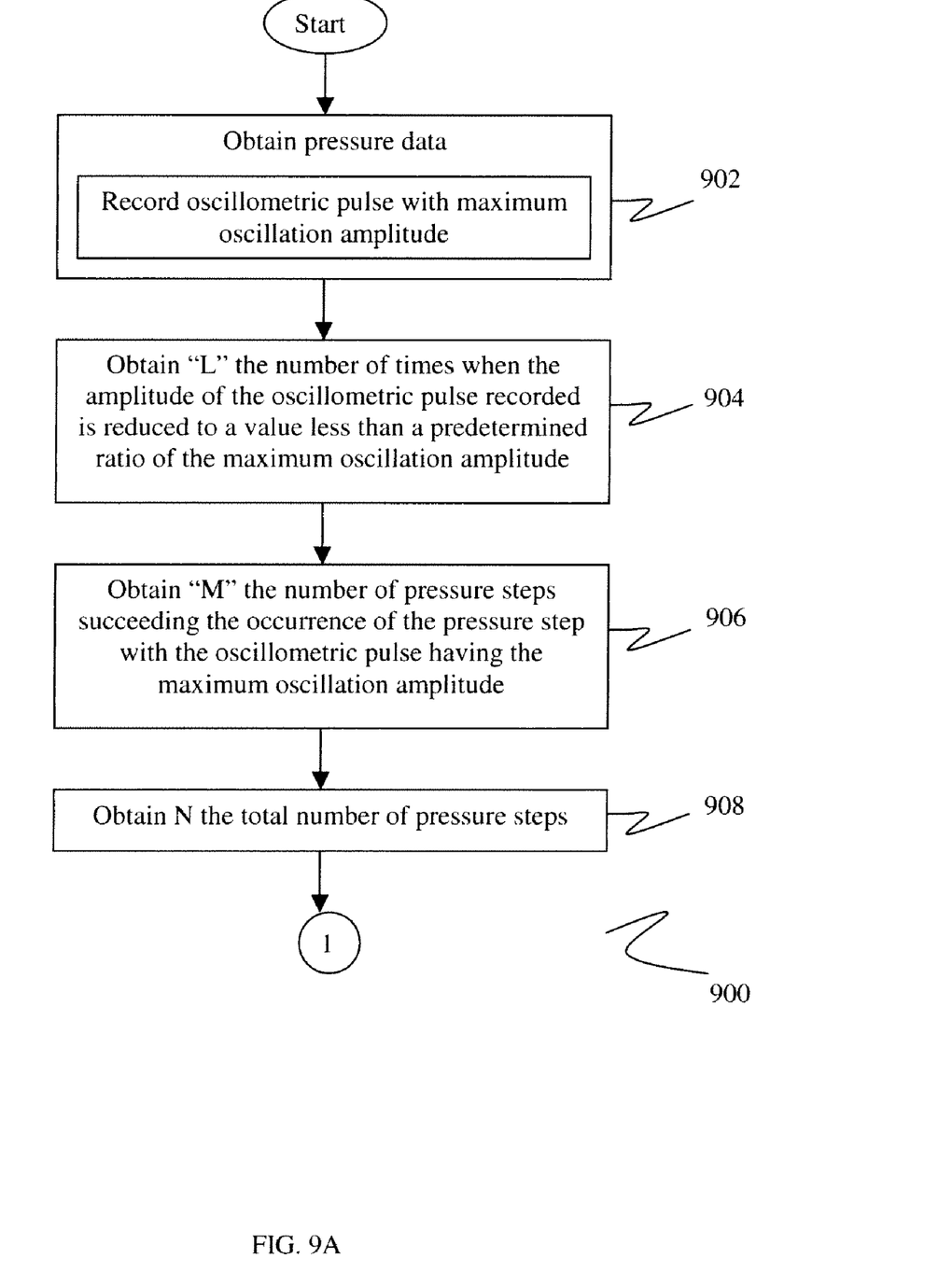
FIG. 9A is a first page of a flowchart describing the method of predicting the termination of cuff pressure variation, as described in one embodiment of the invention.
Figure 9B:
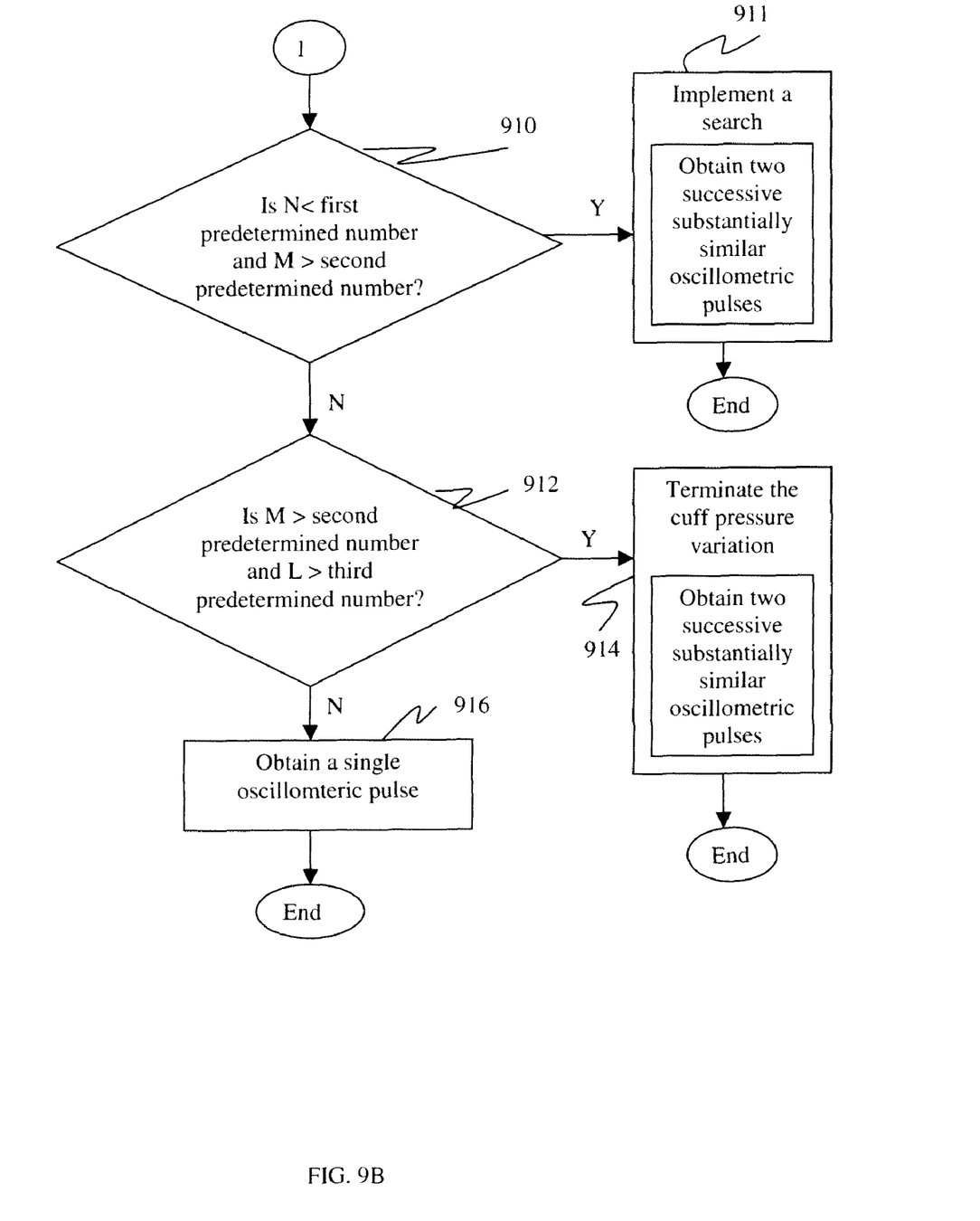
FIG. 9B is a second page of a flowchart describing the method of predicting the termination of cuff pressure variation, as described in one embodiment of the invention.

The method of identifying the pressure steps scheduled for obtaining a single oscillometric pulse comprises implementing a step counter for monitoring the number of pressure steps or cuff pressure variations. The step counter can be employed for counting the number of pressure steps taken so far in the blood pressure determination. Also, depending on the value stored in the step counter, the NIBP system 100 can decide upon the number of oscillometric pulses to be taken in the corresponding pressure step. For example, an odd number stored in the step counter can prompt the NIBP system 100 to take at least two oscillometric pulses and an even number stored in the step counter can prompt the NIBP system 100 to take a single oscillometric pulse or vice versa. The step counter can be reset following a significant inflation or deflation of the blood pressure cuff 102. In addition, the step counter can be used as part of the information monitoring needed to predict the termination of the cuff pressure variation. The following paragraphs in conjunction with FIG. 9, describe the method 900 for predicting the termination of the cuff pressure variation.

The method 900 comprises monitoring the amplitude of each oscillometric pulse recorded while obtaining pressure data in a blood pressure determination process at step 902. Further, maximum oscillation amplitude, which is a maximum among the amplitudes of the oscillometric pulses recorded, can be identified and stored at step 902. The information about the pressure step on which the oscillometric pulse with the maximum oscillation amplitude occurs can be used as part of the information monitoring needed to predict the termination of the cuff pressure variation.

The method 900 further comprises counting "L", the number of times when the amplitude of the oscillometric pulse recorded during the process of the blood pressure determination, is reduced to a value less than a predetermined ratio of the maximum oscillation amplitude at step 904 and counting "M", the number of pressure steps succeeding the occurrence of the pressure step with the oscillometric pulse having the maximum oscillation amplitude at step 906. The method further comprises obtaining the total number of pressure steps "N" at step 908. "N" can be obtained from the step counter. Further, the information about "N", "M" and "L" can be used, as part of the information monitoring needed to predict the termination of the cuff pressure variation or the pressure data collection.

Predicting the termination of the cuff pressure variation comprises making a decision as to whether a selected pressure step can possibly be a final pressure step in the blood pressure determination. Therefore, predicting the termination comprises one of terminating the cuff pressure variation, initiating a search and predicting the occurrence of a future pressure step. In order to select an appropriate option, the method 900 described in FIG. 9 includes two decision-making steps 910 and 912.

At step 910, the total number of pressure steps stored in the step counter "N" is compared to a first predetermined number and the number of pressure steps "M" succeeding the occurrence of the pressure step with the oscillometric pulse having the maximum oscillation amplitude is compared to a second predetermined number. When "N" is less than the first predetermined number and "M" exceeds the second predetermined number, the method proceeds to implement a search at step 911.

The search is a process where the NIBP monitor 100 does not have enough information to compute the blood pressure estimates and therefore causes a significant inflation or deflation of the blood pressure cuff 102 to gather additional information. Following the significant inflation or deflation of the blood pressure cuff 102, the transient baseline effects component versus cuff pressure characteristics is expected to be similar to the graph shown at FIG. 7. Therefore, for the NIBP monitor 100 to be accurate, an appropriate weighting equation is to be used for estimating the transient baseline effects component, which may rely on adjacent pressure steps with more than one oscillometric pulse. In order to accomplish this, the NIBP monitor 100 is provided with additional intelligence to predict the occurrence of a future pressure step, and to complete the determination. Following the decision to carry out the search, the first weighting equation is used for estimating the transient baseline effects component for a first secondary data point following the significant inflation or deflation.

Furthermore, subsequent to making the decision to implement the search, for a pressure step occurring prior to implementing the search, the NIBP monitor is configured to obtain two substantially similar oscillometric pulses at step 911. It should be noted that a secondary data point has at least one preceding primary data point and at least one succeeding primary data point in order to employ one of the weighting equations to estimate the transient baseline effects component for the secondary data point. Therefore, a decision to implement the search is accompanied by obtaining two substantially similar oscillometric pulses. Following the implementation of the search, the NIBP monitor 100 is configured to predict the occurrence of a pressure step in the future in order to decide upon the number of oscillometric pulses to be taken in the existing pressure step.

Referring back to step 910, in an alternative embodiment, when "N" exceeds the first predetermined number or "M" is less than the second predetermined number, the method proceeds to a second decision-making step 912. At step 912, "M" is compared to the second predetermined number and "L" is compared to a third predetermined number. When "M" exceeds the second predetermined number and "L" exceeds the third predetermined number, the method 900 proceeds to terminate the cuff pressure variation at step 914.

In an exemplary embodiment, the first predetermined number is selected to be six and the second predetermined number is selected to be four. This is based on the practical knowledge that the oscillometric pulses recorded during six pressure steps in the blood pressure determination process generally provide sufficient pressure data to estimate the blood pressure parameters. Further, the number of the pressure steps, following the occurrence of the pressure step with the oscillometric pulse having the maximum oscillation amplitude, may not be more than four, for the amplitude of the oscillometric pulse to fall off to a value less than a fixed fraction of the maximum oscillation amplitude.

In another exemplary embodiment, the third predetermined number is selected to be two. This is based on the fact that the amplitude of the oscillometric pulses at the systolic or diastolic blood pressure level is a fixed fraction (ratio) of the maximum oscillation amplitude found at MAP 204. Therefore, irrespective of the technique employed in obtaining the oscillometric envelope data, be it by step inflation or step deflation process, the fall in the amplitude of the oscillometric pulses recorded is observed. However, the value of the first, second and third predetermined numbers may vary.

Following the decision to terminate the cuff pressure variation, an existing pressure step is selected as the final pressure step. Subsequent to the selection of the final pressure step, irrespective of the value stored in the step counter, the value stored in the step counter influencing the number of oscillometric pulses to be recorded in the selected pressure step, the method 900 forces the collection of at least two successive oscillometric pulses (step 914) with typical pulse amplitude matching, pulse period consistency and pulse slope consistency criteria employed to reject the artifacts. Two successive and matched oscillometric pulses are to be obtained on the final pressure step of a blood pressure determination process, irrespective of the indication from the NIBP system 100 to obtain a single oscillometric pulse at the final pressure step. This is based on the fact that there are no additional pressure steps, following the final pressure step, to gather additional oscillometric pulses in order to estimate the transient baseline effects component for the final pressure step.

Further, subsequent to executing the steps 910 and 912 and entering the step 916 as a result of not satisfying at least one condition mentioned in the steps 910 and 912, the method 900 predicts the occurrence of a future pressure step and therefore obtains a single oscillometric pulse at step 916. Thereafter, the NIBP system 100 continues the process of obtaining pressure data and the method 900 is performed each time the pressure data is obtained. Thus, the method 900 continually analyzes the collected pressure data to determine if a selected pressure step may have a single oscillometric pulse and to predict the occurrence of a future pressure step.

In another embodiment, a computer readable storage medium with a plurality of program instructions for execution by the processor 104 of the NIBP monitor 100 so as to monitor blood pressure in a patient is provided. The plurality of program instructions include a routine for obtaining pressure data comprising an oscillatory component and a transient baseline effects component, a routine for constructing a pressure data waveform, a routine for selecting a plurality of data points acquired from the waveform of the pressure data, a routine for generating a non-linear transient baseline effects model based on the plurality of data points, a routine for implementing the non-linear transient baseline effects model to at least partially deduct the transient baseline effects component from the pressure data such that substantially only the oscillatory component remains and a routine for generating an estimate of the blood pressure parameters based on the oscillatory component of the pressure data.

Further, the routine for obtaining pressure data comprises a routine for inflating the blood pressure cuff 102 to a user selectable target pressure, a routine for monitoring the presence of two substantially similar oscillometric pulses at the user selectable target pressure, a routine for deflating the blood pressure cuff 102 upon identifying the occurrence of the substantially similar oscillometric pulses, a routine for monitoring the presence of a single oscillometric pulse, a routine for deflating the blood pressure cuff 102, a routine for repeating the steps of obtaining two matched oscillometric pulses, deflating, obtaining one oscillometric pulse and deflating until a decision to terminate the pressure data collection is made and a routine for predicting the termination of the pressure data collection.

In one embodiment, software and/or firmware (hereinafter referred to generically as "software") can be used to instruct the processor 104 to perform the inventive combination of actions described herein. Portions of the software may have specific functions, and these portions are herein referred to as "modules" or "software modules." However, in some embodiments, these modules may comprise one or more electronic hardware components or special-purpose hardware components that may be configured to perform the same function as the software module or to aid in the performance of the software module. Thus, a "module" may also refer to hardware or a combination of hardware and software performing a function.

In various embodiments described above, an NIBP system 100 capable of monitoring blood pressure parameters and methods of measuring blood pressure parameters are provided.

The method of obtaining pressure data described herein enables the NIBP monitor to obtain a single oscillometric pulse at every alternate pressure step thereby reducing the blood pressure determination time by approximately twenty five percent. Thus, the method provides improvement in the speed of the NIBP monitor without sacrificing accuracy in estimating the blood pressure.

Further, one embodiment describes a method for estimating the transient baseline effects component for the pressure steps that have a single oscillometric pulse.

The methods provided herein reduce the requirement on the number of data points employed to estimate the transient baseline effects model.

In various embodiments of the invention, a system and method for non-invasive blood pressure measurement are described. However, the embodiments are not limited and may be implemented in connection with different applications. The application of the invention can be extended to other areas, for example digital signal processing. The invention provides a broad concept of accurately estimating the noise affecting a signal whilst improving the speed of data collection, which can be adapted in a similar monitoring system. The design can be carried further and implemented in various forms and specifications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of monitoring blood pressure using a blood pressure monitor, the monitor including a blood pressure cuff, the method comprising:

obtaining pressure data comprising an oscillatory component and a transient baseline effects component, wherein obtaining pressure data comprises steps of inflating the blood pressure cuff to a user selectable target pressure;

deflating the pressure in the blood pressure cuff in a stepwise manner by a predetermined pressure amount, identifying at each pressure step in a first sequence of alternate steps of the cuff pressure variation the occurrence of multiple oscillometric pulses, identifying at each pressure step in a second sequence of alternate steps of the cuff pressure variation the occurrence of a single oscillometric pulse and predicting the termination of the deflation of the blood pressure cuff;

constructing a waveform of the pressure data using a processor;

selecting with the processor a plurality of data points acquired from the waveform of the pressure data;

generating a non-linear transient baseline effects model with the processor based on the plurality of data points;

implementing the non-linear transient baseline effects model with the processor to at least partially deduct the transient baseline effects component from the pressure data such that substantially only the oscillatory component remains; and generating an estimate of a blood pressure parameter with the processor based on the oscillatory component of the pressure data, wherein the removal of the transient baseline effects component from the pressure data eliminates a potential source of error and thereby enhances accuracy of the estimated blood pressure parameter.

2. The method of claim 1, wherein generating the transient baseline effects model comprises steps of:

identifying a plurality of data points for estimating the transient baseline effects model, the plurality of data points comprising at least two primary data points and at least one secondary data point;

using an non-linear equation for estimating the transient baseline effects components for the primary data points, the primary data points corresponding to the plurality of oscillometric pulses obtained in a single pressure step; and employing the transient baseline effects components estimated for the primary data points for estimating the transient baseline effects component for the secondary data point, the secondary data point corresponding to a single oscillometric pulse obtained in a single pressure step.

3. The method of claim 2, wherein the non-linear equation is of the type $P_t = Ae^{-(t-t_1)/T} + B$ wherein the variable $P_t$ represents the pressure of the transient baseline effects model at time t, the variable A represents the magnitude of the change in the transient baseline effects model, the variable B represents the equilibrium or steady state pressure of the transient baseline effects model, and the variable T is a time constant.

4. The method of claim 2, wherein employing the transient baseline effects components estimated for the primary data points comprises:

using a first weighting equation for estimating the transient baseline effects component for a first secondary data point, the first secondary data point corresponding to the first single oscillometric pulse obtained in a single pressure step; and using a second weighting equation for determining the transient baseline effects component for one or more secondary data points succeeding the first secondary data point.

5. The method of claim 4, wherein the first weighting equation is of the type $$A_{2a} - A_{21} = A_2 \left( e^{\frac{-(t_{2a}-t_{20})}{T}} - e^{\frac{-(t_{21}-t_{20})}{T}} \right),$$

where $$A_2 = \frac{\left[ \frac{A_{11}-A_{12}}{\left(e^{\frac{-(t_{11}-t_{10})}{T}} - e^{\frac{-(t_{12}-t_{10})}{T}}\right)} \times e^{\frac{-(t_{20}-t_{10})}{T}} + \frac{A_{31}-A_{32}}{\left(e^{\frac{-(t_{31}-t_{30})}{T}} - e^{\frac{-(t_{32}-t_{30})}{T}}\right)} \times \frac{1}{1+e^{\frac{-(t_{30}-t_{20})}{T}}} \right]}{e^{\frac{-(t_{20}-t_{10})}{T}} + \frac{1}{1+e^{\frac{-t_{30}-t_{20}}{T}}}}.$$

6. The method of claim 4, wherein the second weighting equation is of the type $$A_{4a} - A_{41} = A_4 \left( e^{\frac{-(t_{4a}-t_{40})}{T}} - e^{\frac{-(t_{41}-t_{40})}{T}} \right),$$

where $$A_4 = \frac{\left[ \frac{A_{31}-A_{32}}{\left(e^{\frac{-(t_{31}-t_{30})}{T}} - e^{\frac{-(t_{32}-t_{30})}{T}}\right)} + \frac{A_{51}-A_{52}}{e^{\frac{-(t_{51}-t_{50})}{T}} - e^{\frac{-(t_{52}-t_{50})}{T}}} \right]}{2}.$$

7. The method of claim 1, further comprising displaying the estimated blood pressure parameter, wherein the blood pressure parameter comprises systolic blood pressure, diastolic blood pressure and mean arterial pressure.

8. The method of claim 1, wherein the plurality of data points represent consecutive phase points.

9. The method of claim 1, further comprising filtering the pressure data prior to generating the non-linear transient baseline effects model.

10. A non-transient computer readable storage medium having embodied thereon plurality of program instructions for execution by a processor of an NIBP monitor, so as to monitor blood pressure parameters in a patient, the plurality of program instructions including:

a routine for obtaining pressure data comprising an oscillatory component and a transient baseline effects component, wherein the routine for obtaining pressure data comprises a routine for inflating a blood pressure cuff to a user selectable target pressure; a routine for deflating the pressure in the blood pressure cuff in a stepwise manner by a predetermined pressure amount, a routine for identifying at each pressure step in a first sequence of alternate steps of the cuff pressure variation, the occurrence of multiple oscillometric pulses; a routine for identifying at each pressure step in a second sequence of alternate steps of the cuff pressure variation, the occurrence of a single oscillometric pulse and a routine for predicting the termination of the deflation of the blood pressure cuff;

a routine for constructing a waveform of the pressure data;

a routine for selecting a plurality of data points acquired from the waveform of the pressure data;

a routine for generating a non-linear transient baseline effects model based on the plurality of selected data points;

a routine for implementing the non-linear transient baseline effects model to at least partially deduct the transient baseline effects component from the pressure data such that substantially only the oscillatory component remains; and a routine for generating an estimate of the blood pressure parameters based on the oscillatory component of the pressure data, wherein the removal of the transient baseline effects component from the pressure data eliminates a potential source of error and thereby enhances accuracy of the estimated blood pressure parameters.

11. The non-transient computer readable storage medium of claim 10, wherein the routine for generating the transient baseline effects model comprises:

a routine for determining a plurality of data points, the plurality of data points comprising at least two primary data points and at least one secondary data point;

a routine for using a non-linear equation for estimating the transient baseline effects components for the primary data points, the primary data points corresponding to the plurality of oscillometric pulses obtained at a single pressure step; and a routine for employing the transient baseline effects components estimated for the primary data points for estimating the transient baseline effects component for the secondary data point, the secondary data point corresponding to the single oscillometric pulse obtained in a single pressure step.

12. The non-transient computer readable storage medium of claim 11, wherein the routine for employing transient baseline effects components estimated for the primary data points comprises:

a routine for using a first weighting equation for estimating the transient baseline effects component for a first secondary data point, the first secondary data point corresponding to the first single oscillometric pulse obtained in a single pressure step; and a routine for using a second weighting equation for estimating the transient baseline effects component for one or more secondary data points succeeding the first secondary data point.

13. The non-transient computer readable storage medium of claim 10, further comprising a routine for displaying the estimated blood pressure parameters, wherein the blood pressure parameters comprise systolic blood pressure, diastolic blood pressure and mean arterial pressure.

14. The non-transient computer readable storage medium of claim 10, further comprising a routine for filtering the pressure data prior to generating the non-linear transient baseline effects model.

* * * * *